United States Patent
Vuong

(10) Patent No.: US 6,770,585 B2
(45) Date of Patent: Aug. 3, 2004

(54) MOMORDICA COCHINCHINENSIS (SPRENG.) β-CAROTENE AND METHOD

(75) Inventor: Le Thuy Vuong, Davis, CA (US)

(73) Assignee: Vitalea Science, Inc., Davis, CA (US)

(*) Notice: Subject to any disclaimer, the term of this patent is extended or adjusted under 35 U.S.C. 154(b) by 165 days.

(21) Appl. No.: 10/211,814

(22) Filed: Aug. 5, 2002

(65) Prior Publication Data

US 2004/0024275 A1 Feb. 5, 2004

(51) Int. Cl.⁷ ............................. C07C 13/16; C10G 1/04

(52) U.S. Cl. .................... 502/20; 502/240; 502/351; 424/777

(58) Field of Search .................... 585/20, 240, 351; 424/777

(56) References Cited

U.S. PATENT DOCUMENTS 6,261,598 B1 * 7/2001 Runge et al. ............... 424/456

* cited by examiner

Primary Examiner—Elizabeth D. Wood
(74) Attorney, Agent, or Firm—Gray Cary Ware & Freiderich LLP

(57) ABSTRACT

The present invention provides a process to extract oil from *Momordica cochinchinensis* aril to yield an edible oil rich in β-carotene. The process can be carried out without the use of any harmful organic solvents, and provides products containing other carotenoids, such as lycopene, and fiber and vitamin E. This invention provides a bioavailable and stable source of β-carotene, a pro-vitamin A carotenoid, in areas where vitamin A deficiency exists. Products derived from this invention serve as a safe source of antioxidants and nutritional supplement for human and animal consumption, and for the pharmaceuticals and cosmetics industries as well as providing a suitable, effective food additives and colorants.

8 Claims, No Drawings

MOMORDICA COCHINCHINENSIS (SPRENG.) β-CAROTENE AND METHOD

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING

Not Applicable

BACKGROUND OF THE INVENTION

1. Field of Invention

The present invention relates to food, food supplements, animal feedstuffs, human foodstuffs, pharmaceutical and cosmetic preparation, particularly of a process to produce a food that can improve health and prevent diseases.

2. Prior Art

*Momordica cochinchinensis* Spreng (spiny melon) is indigenous to Southeast Asia, and not commonly seen in this country. Descriptions of the plant can be found in several publications (Bailey, Heiser, Herklots and Perry). Medicinal use of *Momordica cochinchinensis* seeds was described by Nguyen, and by Vuong (Vuong, 1998). Concentrations of total carotenoid in *Momordica cochinchinensis* can be found in a publication by West & Poortvliet. A publication by Vuong described the plant and discussed its use in improving vitamin A status of children in Vietnam (Vuong, 2000). Another publication by Vuong et al. described a supplementation trial of rice mixed with *Momordica cochinchinensis* pulp to improve plasma retinol and beta-carotene of preschoolers in Vietnam (Vuong et al., 2002).

Beta-carotene is among hydrocarbon carotenoids with antioxidative activities (Krinsky). According to epidemiological and animal studies, beta-carotene plays an important role in the prevention of cancer (Bertram, Carughi, Krinsky, Narisawa et al., Poppel and Goldbohm). β-carotene as a provitamin A carotenoid is essential in regions of the world where vitamin A deficiency exists and food rich in retinol is not economically available. It would be a significant advancement in the art to obtain β-carotene from aril of *Momordica cochinchinensis* fruits and to provide an economical process to produce food products high in beta-carotene.

Beta-carotene is abundant in fruits, vegetables and some animals (Britton). Red palm oil, oil extract from palm fruits is the only food oil that contains significant amount of beta-carotene (Nagendran et al., Choo et al.). Commercial production, composition and application of red palm oil have been widely published (Kritchevsky, Scrimshaw, Rao, Manorama & Rukmini, Nagendran et al.). Rao and other authors reported positive results of studies using red palm oil to improve vitamin A status of children in India and Africa (Rao, Stuijvenberg and Benade). Efficiency of the conversion of intake beta-carotene into vitamin A depends on the amount of available beta-carotene in the body or the bioavailability of beta-carotene and physiological status of the host (Dimitrov et al., Goodman). Absorption of dietary beta-carotene is effected by many factors (de Pee et al., Van Vliet et al., Dimitrov et al.). Oil facilitates the absorption and transport of beta-carotene and thus increases its bioavailability (Goodman).

CITED REFERENCES

1. Bailey LH. The Garden of the Gourds. New York: The Macmillian Company, 1937.
2. The Gourd Book. Norman: University of Oklahoma Press, 1979.
3. Herklots GAC. Vegetables in South-East Asia. London: George Allen & Unwin LTD, 1972.
4. de Pee S, West C E, Permaesih D, Martuti S, Muhilal, Hautvast J G A F. Orange fruit is more effective than are dark-green, leafy vegetables in increasing serum concentration of retinol and β-carotene in schoolchildren in Indonesia. Am J Clin Nutr 1998; 68:1058–67.
5. Britton, G. Carotenoids. In Natural Food Colorants; Hendry, G. A. F., Houghton, J. D., Eds., Blackie: Glasgow, U.K. 1992; p 280.
6. Dimitrov N V, Meyer C, Ullrey D E, Chenoweth W, Michelakis A, Malone W, Boone C, Fink G. Bioavailability of β-carotene in humans. Am J Clin Nutr 1988; 48:298–304.
7. Goodman D. The intestinal absorption and metabolism of vitamin A and β-carotene in man. J Clin Invest 1966; 45:1615–23.
8. Krinsky N., Antioxidant functions of carotenoids. Free Radical Biology & Medicine. Vol. 7, pp. 617–35, 1989.
9. Kritchevsky D. Impact of red palm oil on human nutrition and health. Food and Nutrition Bulletin, 21:2, 2000, pp. 182–88.
10. Manorama R, Rukmini C. Effect of processing on beta-carotene retension in crude palm oil and its producs. Food Chem 1991; 42: 253–64.
11. Manorama R, Brahmam GNV, Rukmini C. Red palm oil as a source of beta-carotene for combating vitamin A deficiency. Plant Foods Hum Nutr 1996; 49:75–82.
12. Nagendran B., Unnithan R. R., Choo Y. M., and Kalyana Sundram. Characteristics of red plam oil, a carotene- and vitamin E-rich refined oil for food uses. Food and Nutrition Bulletin, Vol. 21, Number 2, June 2000, pp. 189–201.
13. Poppel G. & Goldbohm R. Epidemiologic evidence for β-carotene and cancer prevention. Am J clin Nutr, 1995; 62 (suppl):1393S-402S.
14. Rao N. Potential use of red palm oil in combating vitamin A deficiency in India. Food and Nutrition Bulletin, 21:2, 2000, pp. 202–11.
15. Scrimshaw N. Nutritional potential of red palm oil for combating vitamin A deficiency. Food and Nutrition Bulletin, 21:2, 2000, pp. 195–201.
16. Van Vliet T. Absorption of β-carotene and other carotenoids in humans and animal models. Eur J Clin Nutr 1996; 50(Suppl 3):S32-7.
17. Thieme J. G. Coconut Oil Processing. Agricultural Development Paper No. 89. Food And Agriculture Oganization of the United Nations, Rome, 1968.
18. Nagendran B., Unnithan U. R., Choo Y. M., and Kalyana Sundram. Characteristics of red palm oil, a carotene- and vitamin E-rich refined oil for food uses. Food and Nutrition Bulletin, 21:2, 2000, pp. 189–201.
19. Chandler, L. A., and Schwartz S. J., HPLC separation of cis-trans carotene isomers in fresh and processed fruits and vegetables. J. Food Sci. 1987, 5(3), 669–72.
20. Choo, Y. M. et al.: "Production of Palm Oil Carotenoid Concentrate And Its Potential Application in Nutrition", Lipid-Soluble Antioxidants, 1992, pp. 243–254, XP-002120457.
21. Carughi A. et al. "Plasma Carotenoid Concentrations Before and After Supplementation With a Carotenoid Mixture", American Journal of Clinical Nutrition, vol. 59, No. 4, April, 1994, pp. 896–899, XP002120458.
22. Bertram J., "The chemoprevention of cancer by dietary carotenoids: studies in mouse and human cells," Pure & Appl. Chem., vol. 66, No. 5, pp. 1025–1032 (1994).
23. Krinsky N, "Carotenoids and Cancer: Basic Research Studies," Nat. Antioxid. Health Dis., pp. 239–261 (1994).
24. Bertram J, "The chemoprevention of cancer by dietary carotenoids: studies in mouse and human cells," Oxid, Stress and Aging, pp. 221–235 (1995).
25. Le T. Vuong. Underutilized beta-carotene-rich crops of Vietnam. Food and Nutrition Bulletin, Vol. 21, No. 2, June 2000.
26. Le T. Vuong, Stephen R Dueker, Suzanne P. Murphy. Plasma beta-carotene and retinol concentrations of children increase after a 30-d supplementation with the fruit *Momordica cochinchinensis* (gac). Am J Clin Nutr 2002; 75:872–9.
27. Narisawa et al., "Inhibitory effects of natural carotenoids, .alpha.-carotene, beta.-carotene, lycopene and lutein, on colonic aberrant crypt foci formation in rats," Cancer Letters, vol. 107, pp. 137–142 (1996).
28. Nguyen D V. Medicinal Plants of Vietnam, Cambodia and Laos. Westminster, Calif.: Mekong Printing, 1998.
29. Perry L. M. Medicinal Plants of East and Southeast Asia, Attributed Properties and Uses. Cambridge: The MIT Press, 1980.
30. Vuong, L. T. Xoi Gac, a rice preparation containing beta-carotene from *Momordica cochinchinensis* Spreng (gac), for the prevention of vitamin A deficiency in northern Vietnam. Ph. D. Dissertation, University of California at Davis, 1998.
31. West C E. Poortvliet E J. The Carotenoid Content Of Foods With Special Reference To Developing Countries. Washington D.C.: USAID-VITAL, 1993.

OBJECTS AND ADVANTAGES

The objects of this invention include the process to produce an edible oil extract containing beta-carotene, lycopene, vitamin E, from the aril of *Momordica cochinchinensis* Spreng (spiny melon) and the use of this oil in food, and nutritional supplement for human and animal consumption, and for the pharmaceuticals and cosmetics industries.

Spiny melon is indigenous to Southeast Asia. The plant can be cultivated either from seeds or root tubers. The aril of spiny melon contains a significant amount of carotenoids, particularly beta-carotene and lycopene, and oil. In one of the embodiments of this invention, oil is extracted from dried aril of spiny melon. The oil contains beta-carotene, lycopene and vitamin E. The process does not involve any organic solvent and thus the oil is safe for human and animal consumption. According to epidemiological and animal studies, carotenoids play an important role in the prevention of cancer, and heart disease. β-carotene as a provitamin A carotenoid is essential in regions of the world where vitamin A deficiency exists and food rich in retinol is not economically available. It would be a significant advancement in the art to attain beta-carotene and lycopene from spiny melon especially in its own oil, which can improve absorption and transport of carotenoids.

BRIEF SUMMARY OF THE INVENTION

The present invention is directed to a method of obtaining carotenoids from *Momordica cochinchinensis* aril in an oil extract and in the dried aril. In one currently preferred embodiment of the method, a quantity of *Momordica cochinchinensis* aril is obtained. Aril is removed from seeds. The wet aril can be used as it is, or dried. Drying can be accomplished using conventional drying techniques, such as freeze drying, drum drying, tray drying, sun drying, and spray drying. Drying is preferably in low heat and closed chamber to avoid degradation of carotenoids. In one currently preferred embodiment of the method, wet aril is dried in an electric powered drying box under 60° C. The dried *Momordica cochinchinensis* aril preferably has a moisture content in the range of 10–15% by weight. Dried aril can be stored in sealed, dark container for up to 1 year without significant degradation of carotenoids. In one currently preferred embodiment of the method, dried aril is heated slightly before pressing for oil. Heating improves yield of oil, and separation of carotenoids from the plant protein. In another preferred embodiment of the method, an oil expeller is used to produce oil extract. Oil produced can be filtered by using a leaf filter, or centrifuge decanter, or letting the oil rest in a large container overnight, separate out the residue, and then letting the oil go through a leaf filter to reduce water content. Oil extract of *Momordica cochinchinensis* aril contains from 3000 to 6500 ppm of carotenoids by weight, of which 45–75% are β-carotene. Oil produced from *Momordica cochinchinensis* aril should be stored in sealed and dark container to avoid rapid degradation and/or oxidation of carotenes. Oil can be kept up to 2 years with minimum loss of β-carotene and without any added preservatives.

BRIEF DESCRIPTION OF TH SEVERAL VIEWS OF THE DRAWING (Not Applicable)

DETAILED DESCRIPTION OF THE INVENTION

The present invention is directed to carotenoids fom the aril of *Momordica cochinchinensis* fruit and to the process of extracting and purifying the oil extract.

In a currently preferred process of producing *Momordica cochinchinensis* oil extract, the ripen fruit is either hand picked or by mechanical equipment. The fruit can be harvested when its color becomes orange or red. After harvested, fruits can be kept at room temperature for about 2 weeks. The ripe fruit is preferably placed in straw lined containers for further processing and transport. The containers can optionally be stored under refrigerated conditions prior to further processing. The fruit used in the production of oil is inspected for spoilage. Spoiled fruit is separated from the acceptable fruit. The fruit is thoroughly cleaned before any processing occurs.

The processing method for *Momordica cochinchinensis* aril oil includes seeding, drying, pressing, separation of water, and packaging was designed to retain maximum amount of β-carotene, minimum water activity and low rancidity value in the oil.

Seeding and Drying

*Momordica cochinchinensis* fruit aril contains between 17,000–35,000 μg/100 g of β-carotene depending on ripeness of the fruit. The amount of lycopene in gac fruit aril varies between 2 to 5 times that of β-carotene (35,000–175,000 μg/100 g), also depending on ripeness of the fruit. About 40% of the dry weight is oil.

The first step in the oil extraction process is scooping out all the aril from the cavity of the fruit into a large container. Separation of seeds from the wet aril can be done mechanically or manually. To remove the seeds manually, the preferred method is to dry the aril by using a variety of methods, including freeze drying, drum drying, tray drying, or sun drying. If a conventional electric powered drying box, or warming oven is used, the wet aril at first is spread on a drying tray. The tray is best made of stainless-steel wire, gaps should not be larger than one inch square. The trays are then placed in the drying box for about 1 hr under 60 deg. C. until the surface of the aril is no longer sticky. At this temperature, the aril can be dried quickly, however, the heat is not high enough to destroy carotenoids. Drying box or warming oven should be closed and dark, as light will also destroy carotenes. The aril can also be covered by clean cloth and sun dried for 4–5 hours, or on a pan over low flame for about 1 hour, however these techniques are expected to incur higher loss of light, heat, and oxygen sensitive carotenoids. Apparently, seeds can also be removed from the wet aril (without drying), however this takes a considerable longer time, and loss of materials is higher. Drying aril before seeding has shown to speed up the seeding process, and reduce water which is necessary for the oil production. Dried aril is then peeled open, and the seeds are removed. The aril after seeded still contains a significant amount of moisture. The oil produced will contain too much water. Seeded aril should be dried again in drying oven under 60 deg C. until moisture content is reduced to about 12–15%. Depending on the size of the drying oven, this step can take up to 2 hours for about 60 kg of fruits. Carotenoids can also be removed from seeds and aril by mixing the aril with alcohol or any organic solvents (ethanol, THF), however, this method is not preferable as it is neccessary to remove all potentially toxic solvents when the oil or aril is used as a food ingredient.

Pressing and Oil Separation

Pressing can be done with a continuous expeller or a small single expeller. If an electric powered oil press is not available, a manual screw press or semi-manual, hydrolic oil press can be used. If a boiler is not attached with the expeller, aril should be warmed slightly in oven (<60 deg C.), for about 10 min, since warming the aril will increase oil yield. Oil yield by the medium size continuous oil expeller is about 20–22%, and of the manual press is about 10% dried weight of aril. The oil produced can be settled in a large container overnight to separate out residue, and further purified by filtering. The filtering equipment preferably consists of, but is not limited to, a centrifuge decanter, a screen filter, a filter press, a leaf filter, reverse osmosis filtration, and any other standard commercial filtration devices. Oil produced by this process should contain between 3000–6500 ppm of total carotenoids, 2500–4500 ppm β-carotene, 500–2500 ppm lycopene, and 150–350 ppm vitamin E (alpha tocopherol). The oil produced by the described process has 0.29% of moisture, pH=4.32, and 0.10% of free fatty acid as oleic. Peroxide Value of the oil is less than 1 meq/kg. Since the oil contains a significant amount of carotenoids, it has an intense red color. It has no odor and a mild nutty flavor. Other available methods can be used to bleach the oil, and/or deodorize to improve palatability or marketability. Oil should be kept in dark, sealed containers and refrigerated to prevent degradation and/or oxidation of carotenoids. If properly stored, oil can be kept for at least 2 years with minimum loss of carotenes, and undetectable rancidity. Oil from *Momordica cochinchinensis* aril is extremely rich in β-carotene and contains a significant amount of vitamin E. The oil is high in polyunsaturated fatty acids, and low in saturated fatty acids. *Momordica cochinchinensis* oil can be used in a variety of applications, including, but not limited to cooking oil, salad oil, condiments, seasonings, food colorants, dietary supplements, cosmetics including soaps, skin oil, and animal feedstuff.

The following tables demonstrate nutritional values of oil extract of *Momordica cochinchinensis*. Values presented are representative of quantitative analyses for this invention, but not inclusive or absolute, since nutrient contents of fruits may vary depending on ripeness, growing regions or climate and post-harvest handling and processing.

TABLE 1

Carotenoid profile of oil produced from Momordica cochinchinensis aril

| Carotenoids | % of total carotenoids |
|---|---|
| Alpha-carotene | 13.02 |
| β-carotene | 49.08 |
| Phytoene | 2.36 |
| Lutein | 7.07 |
| Lycopene | 10.73 |
| Other minor carotenes | 17.74 |

TABLE 2

Fatty acid profile of oil produced from Momordica cochinchinensis aril

| Type of fatty acids | Percentage of total fats by weight |
|---|---|
| Myristic Acid (C14:0) | 0.13% |
| Palmitic Acid (C16:0) | 18.63% |
| Palmitoleic Acid (C16:1) | 0.15% |
| Stearic Acid (C18:0) | 3.04% |
| Oleic Acid (C18:1) | 31.63% |
| Linoleic Acid (C18:3) | 16.76% |
| Arachidic Acid (C20:0) | 0.12% |
| Linolenic Acid (C18:3) | 0.26% |

TABLE 3

Nutrition facts of oil produced from Momordica cochinchinensis aril

Serving Size 1 teaspoon (5 mL)
Sevings Per Container (4 oz) 26

| Amount per serving | | % Daily Value* |
|---|---|---|
| Calories 28.5 | Fat Cal. 28.5 | |
| Total Fat 3.3 g | | 1 |
| Saturated Fat | 1 g | |
| Polyunsaturated Fat | 0.8 g | |
| Monounsaturated Fat | 1.5 g | |
| Cholesterol | 0 mg | |
| Sodium | 0 mg | |
| Total Carbohydrate | 0 mg | |
| Protein | 0 mg | |
| β-carotene | 14.5 mg | |
| lycopene | 2.6 mg | |
| Vit A (retinol activity equivalent) | 7000 : g RAE | 1000 |
| Vit E | 0.65 mg | 0.1 |
| This product is a good source of vitamin A and other antioxidants | | |

*Percent Daily Values are based on a 2000 calorie diet.

EXAMPLES

The following examples are given to illustrate various embodiments which have been made or may be made in accordance with the present invention. These examples are given by way of examples only, and it is to be understood that the following examples are not comprehensive or exhaustive of the many types of embodiments of the present invention which can be prepared in accordance with the present invention.

Example 1

A marinade sauce containing *Momordica cochinchinensis* oil (Mc. Oil) was prepared having the following ingredients

| Ingredients | Amount |
|---|---|
| Mc. Oil | 1/12 cup |
| Olive Oil | 1/6 cup |
| Balsamic Vinegar | 1/3 cup |
| Dried oregano | ½ teaspoon |
| Dried rosemary | ½ teaspoon |
| Fresh garlic, minced | 2 cloves |
| Green onion, diced | 4 sprigs |
| Salt | ¼ teaspoon |

Example 2

A β-carotene rich skin oil made from *Momordica cochinchinensis* oil (Mc. oil)

| Ingredients | Amount |
|---|---|
| Mc. oil | 10 ml |
| Vitamin E oil | 5 ml |
| Lavender oil | 1 ml |

The present invention may be embodied in other specific forms without departing from its essential characteristics. The described embodiments are to be considered in all respects only as illustrative and not restrictive. The scope of the invention is, therefore, indicated by the appended claims rather than by the forgoing description.

What is claimed is:

1. A process to obtain carotenoids from the aril of the fruit *Momordica cochinchinensis* to yield an oil rich in carotenoids including β-carotene, lycopene, other oil soluble nutrients such as vitamin E, comprising the following steps:

obtaining a quantity of ripen fruits of *Momordica cochinchinensis* plant;

collecting aril (and seeds) from the cavity of the fruits;

separating aril from seeds.

2. A process as claimed in claim 1, further comprising the step of drying the wet aril, either by freeze drying, drum drying, tray drying, sun drying, or spray drying.

3. A process as claimed in claim 1, further comprising the step of extracting oil from the aril, either by cold pressing using a manual, semi-manual, a mechanical oil press, super-critical $CO_2$ fluid extraction, or by chemical extraction using organic solvents (ethanol, methanol, tetrahydrofuran).

4. A process as claimed in claim 1 by which the oil produced contains from 3000 to 6500 ppm (mg/kg) of total carotenoids.

5. A process as claimed in claim 1 by which the oil produced contains from 2500 to 4500 ppm of β-carotene.

6. A process as claimed in claim 1 by which the oil produced contains from 400 to 1000 ppm of lycopene.

7. A process as claimed in claim 1 by which the oil produced contains from 100 to 250 ppm of total vitamin E.

8. A process as claimed in claim 1, further comprising the step of filtering, deodorizing and/or bleaching the oil using available equipments and published methods to improve palatability and marketability.

* * * * *